United States Patent [19]

Wilhoit

[11] Patent Number: 5,236,561
[45] Date of Patent: Aug. 17, 1993

[54] PROCESS FOR THE PREPARATION OF DICARBOXYLIC ACID

[75] Inventor: Eugene D. Wilhoit, Victoria, Tex.

[73] Assignee: E. I. Du Pont de Nemours and Company, Wilmington, Del.

[21] Appl. No.: 868,324

[22] Filed: Apr. 14, 1992

[51] Int. Cl.$^5$ .............................................. C25B 3/02
[52] U.S. Cl. ........................................ 204/78; 204/86; 204/91; 204/93; 204/96; 204/59 R
[58] Field of Search .................... 204/78, 59 R, 86, 91, 204/93, 96

[56] References Cited

U.S. PATENT DOCUMENTS

| | | | |
|---|---|---|---|
| 3,459,644 | 8/1969 | MacLean et al. | 204/80 |
| 4,647,349 | 3/1987 | Kreh et al. | 204/78 |
| 5,026,461 | 6/1991 | Davis et al. | 204/59 R |

Primary Examiner—John Niebling
Assistant Examiner—Kishor Mayekar

[57] ABSTRACT

A process for the production of dodecanedioic acid by oxidation of cyclododecene using a two liquid phase system comprised of valeric acid and aqueous cerium solutions containing nitrates and bisulfates in dilute nitric acid in which ruthenium tetroxide and lower oxides are dissolved or suspended. In this process cyclododecene is fed directly into the liquid phases which are continuously mixed and contained in an electrolytic cell loop operating at greater than 1.5 v in which the cerium +3 is oxidized to cerium +4 at the anode in a continuous fashion simultaneously with the ruthenium tetroxide oxidation of cyclododecene in the valeric acid. The cerium +4 regenerates the ruthenium tetroxide—simultaneously and in parallel with the other redox reactions. The process is also applicable to oxidation of cyclohexene to adipic acid.

10 Claims, 1 Drawing Sheet

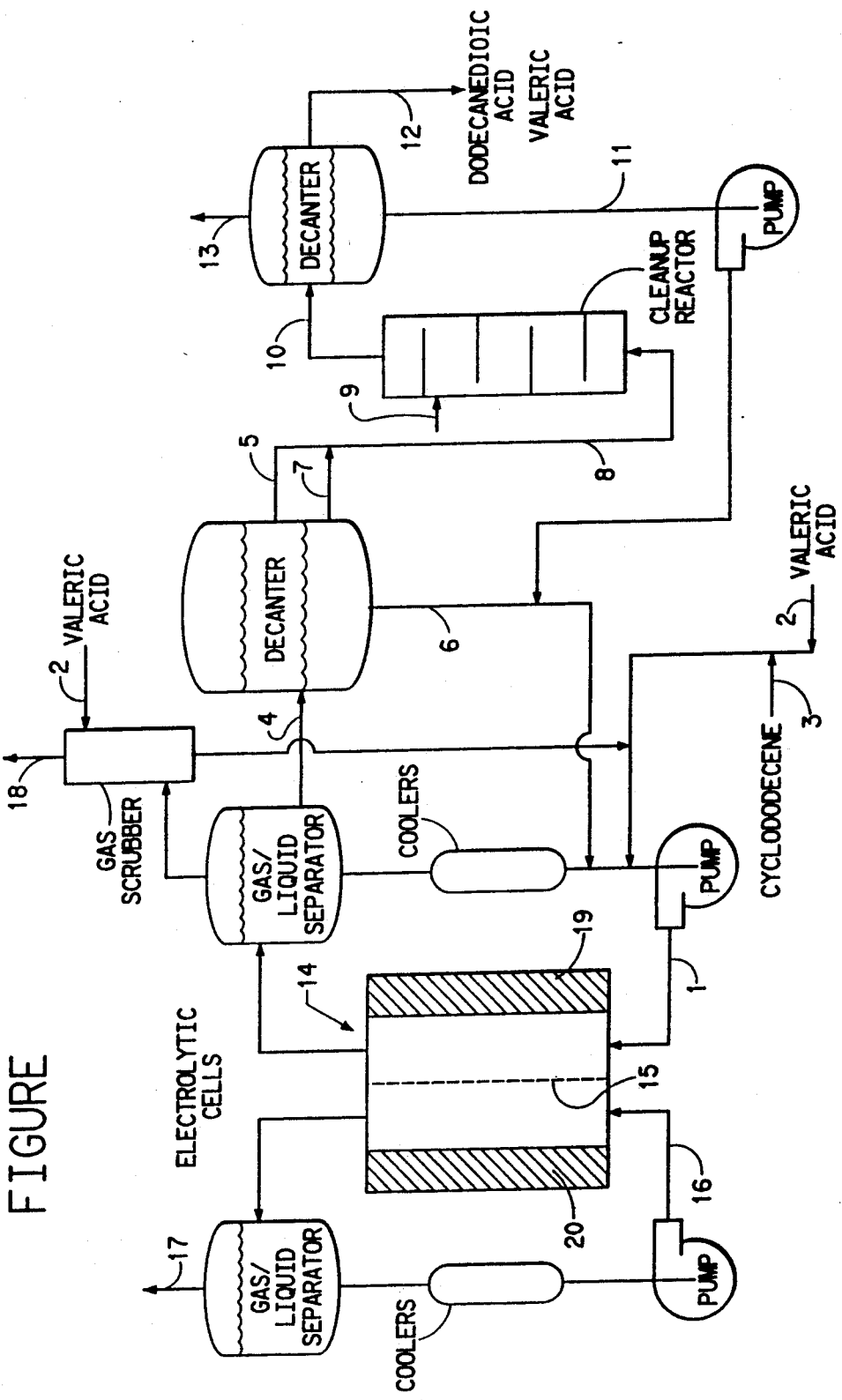
FIGURE

5,236,561

PROCESS FOR THE PREPARATION OF DICARBOXYLIC ACID

FIELD OF THE INVENTION

This invention relates to the production of dicarboxylic acid by oxidation of a cyclic olefin within an electrolytic cell loop. The electrolytic oxidation of cerium +3 to cerium +4 occurs simultaneously and in parallel with the ruthenium tetroxide oxidation of cyclic olefin to dicarboxylic acid. The steady state and continuous conditions are such that the ruthenium tetroxide is regenerated by cerium +4 which is maintained in the range of 0.04N to 0.4N in an aqueous phase by electrolytic oxidation in the anode compartment of an electrolytic cell. The invention is particularly well suited to the production of dodecanedioic acid by the oxidation of cyclododecene.

BACKGROUND OF THE INVENTION

Dodecanedioic acid is commerically prepared by the air oxidation of cyclododecane thus forming cyclododecanol or cyclododecanone. These compounds are then oxidized to dodecanedioic acid by nitric acid. Such a process is disclosed in U.S. Pat. No. 3,637,832.

The oxidation of olefins to aldehydes, ketones and carboxylic acids by the use of ruthenium and cerium salt is disclosed in U.S. Pat. No. 3,459,644 to MacLean et al.

U.S. Pat. No. 5,026,461 to Davis et al. discloses preparation of dodecanedioic acid by the oxidation of cyclododecene by the use ruthenium and cerium salts in a two phase mixture.

The oxidation of saturated cyclohydrocarbons to dioic acids using ruthenium tetroxide with a two-phase system in which the oxidation takes place in the organic phase and the ruthenium dioxide formed in the organic phase is oxidized to ruthenium tetroxide by sodium hypochlorite in the aqueous phase is disclosed in *J. Org. Chem.*, Vol. 40, No. 17, 1975 on pp. 2539-40 by Spitzer et al.

The oxidation of alcohols to carbonyl compounds using a two-phase system employing ruthenium tetroxide as the oxidizing agent in the organic phase, and in which the ruthenium dioxide formed is oxidized indirectly by electrolysis in the aqueous phase back to the tetroxide is disclosed in *J. Org. Chem.*, Vol. 51, pp. 155-161, (1986).

The electrolytic oxidation of cerium +3 ions to cerium +4 ions, and the use of cerium +4 ions as the oxidizing agent in the oxidation of aromatic compounds to carbonyl containing compounds in methanesulfonic acid is disclosed in U.S. Pat. No. 4,639,298 to Kreh.

SUMMARY OF INVENTION

The present invention is a process for oxidation of a cyclic olefin to a dicarboxylic acid which comprises adding the cyclic olefin to a two phase mixture comprising (a) an aqueous phase containing Ce(+4) and Ce(+3) cations, at least one anion selected from the group consisting of nitrate, and bisulfate and dissolved ruthenium tetroxide and (b) an organic phase containing an acid selected from the group consisting of butyric acid, valeric acid, hexanoic acid, and 2-ethyl hexanoic and mixtures of such acids and dissolved ruthenium tetroxide, while subjecting the mixture to electrolytic anodic oxidation at at voltage greater than 1.5 volts at a temperature in the range of about 25 to 85 degrees C.

The present invention uniquely features the simultaneous oxidation of cyclic olefin, e.g., cyclododecene, by ruthenium tetroxide, regeneration of $RuO_4$ by $Ce+4$, and anodic oxidation of $Ce+3$ to $Ce+4$ within an electrolytic cell operating in a continuous and steady state manner. This mode of operation using valeric acid and dilute (10%) solutions of nitric acid and $Ce+4$ in the 0.04-0.4N range, afforded very high current efficiencies ($Ce+3 \rightarrow Ce+4$) while maintaining very high yields (80%) of dicarboxylic acid, e.g., dodecanedioic acid. The invention has advantages over processes with separate organic reactors in series with separate electrolytic cells that use expensive acids, such as methanesulfonic acid, combined with handling very large volumes of cerium solutions per pound of reactant, e.g., U.S. Pat. No. 5,026,461 and U.S. Pat. No. 4,647,349.

This invention provides an improved process for oxidation of a cyclic olefin to a dicarboxylic acid, e.g., cyclododecene to dodecanedioic acid, by the use of ruthenium tetroxide and cerium +4 within an electrolytic cell loop. The improvement embodies the use of low cost nitric acid (compared to costly methanesulfonic) and combines the organic reaction and electrochemical reaction in the cell loop proper.

Further reduction in power cost and investment capital can be obtained with this process if bisulfate, $HSO_4-$, is present in combination with dilute nitric acid and cerium nitrate. The preferred ratio of $NO_3-$ to $HSO_4-$ is 1-2/1 on a molar basis but could range from 0.5-5/1.

Cerium solutions containing bisulfates having a pH less than 2 also can be used in this invention and has cost advantages over methanesulfonic process described in the prior art.

Process parameters for this process can be varied over a range without greatly affecting the embodiments and advantages of this invention. Temperature is optimum in the range 40°-60° C. but could range from 25°-75° C. Higher temperatures generally produce more by-products and result in less overall energy efficiencies. Pressure is not particularly important and will normally be in the range of 1-5 atm. for convenience of operation. Concentration of total cerium usually is in the range 0.1 to 1.0N but preferably in the range of 0.3-0.8N. A key advantage of this process is that the cerium +4 concentration never needs to be much above 0.1N for excellent chemistry, high electrical efficiency, low capital cost and low operation cost. The other prior art [taught by U.S. Pat. No. 4,639,298, U.S. Pat. No. 5,026,461] emphasized the need for high solubility of cerium salts and high concentrations of cerium +4 to reduce handling and equipment costs. This process improvement circumvents these high costs.

Valeric acid is the preferred organic phase for the ruthenium tetroxide oxidation of cyclododecene although butyric acid can be used as a mixture with valeric or used separately. Other acids that may be use include: hexanoic acid, and 2-ethyl hexanoic and mixtures of such acids.

Ruthenium tetroxide in the organic phase, e.g., valeric acid phase, reacts with the feed cyclic olefin, e.g., cyclododecene to form the dicarboxylic acid, e.g., dodecanedioic acid, and to ensure complete conversion, an excess (>2 moles $RuO_4$/1 mole cyclododecene are required) of ruthenium should be present at all times. This can be accomplished by appropriate adjustments to the concentration of ruthenium, electrolytic cell parameters, $Ce+4$ concentration and cyclododecene feed rate. Normally the ruthenium concentration in the two phase mixture is 100-300 ppm and with Ce +4 concentration above 0.05N most of the ruthenium is dissolved in the organic phase as $RuO_4$. If the feed rate of cyclododecene is too high the cerium +4 concentration will drop and conversely increase if the feed rate is too slow (assuming constant cell conditions). Adjustments are readily made to achieve the desired steady state conditions.

The dicarboxylic acid product is dissolved in the organic phase that is removed from the circulating anode loop. Since the aqueous phase is normally 5-10 times the volume of organic phase most of the aqueous phase is returned directly to the anode after decantation. The organic acid phase and a small portion of the aqueous phase are removed for further processing. Ruthenium tetroxide in the organic phase and Ce +4 in the aqueous phase are reduced with a suitable reducing agent ($H_2O_2$, oxalic acid, nitrites), and most of the ruthenium is transferred back to the aqueous phase which is returned to the cell loop.

The organic phase with the dicarboxylic acid and by-products is sent to product refining and organic phase recovery units. Crystallization of crude dicarboxylic acid and distillation of the organic phase for recycle are typical operations used in this process but other unit operation could be practiced.

DESCRIPTION OF THE DRAWING

The drawing shown in the FIGURE is a flow diagram of the process for oxidizing cyclododecene to dodecanedioic acid.

DETAILED DESCRIPTION OF THE INVENTION

A specific process for oxidation of cyclododecene by the use of ruthenium tetroxide, cerium solutions containing nitrates with or without bisulfates, in dilute nitric acid in an electrochemical cell is readily understood by reference to the FIGURE.

A two phase mixture, 1, of aqueous solution containing ruthenium tetroxide and/or lower oxides, cerium+3 and cerium +4 salts (nitrates/bisulfates) and dilute nitric acid (3-10% by weight) and valeric acid containing dissolved cyclododecene is continuously circulated through electrolytic cell, 14, operating at 1.5-5.0 volts. At steady state the cerium +4 concentration is in the range 0.02N-0.5N and preferably 0.1-0.2N. Valeric acid, 2, and cyclododecene, 3, are fed to the cell loop. The aqueous solution is saturated with valeric acid at 25°-75° C. and a valeric acid phase is present (usually about 10% of the aqueous phase by volume but can range from 3-30%). The term "cell loop" as used in this specification means the electrolytic cell 14, and the associated conduits, the gas/liq. sep., the cooler, and pump as illustrated on the left hand portion of the FIGURE. At steady state sufficient liquid mixture, 4, is removed from the cell loop, so that the valeric acid removed is equal to the valeric acid fed along with the products of the oxidation (mainly dodecanedioic acid). The valeric acid phase, 5, is decanted from the larger aqueous phase, 6, which is returned to the cell loop. A small portion (usually 10-20%) of the aqueous phase, 7, is removed from the loop and is re-contacted with the previously decanted valeric phase, 5, to form stream, 8. The volume ratio of the valeric phase, 5, to the purged aqueous phase, 7, is usually 1/1 but can vary by a factor of two either way, e.g., 0.5/2 or 2/0.5. Preferably a vessel, 9, that has plug flow characteristics is used for this re-contacting but a back mixed vessel could be used. A reducing agent (e.g. $H_2O_2$, oxalic acid, nitrites) is usually added at the end of the plug flow vessel, 9, to complete the reduction of Ce +4 which is advantageous in lowering the ruthenium content in the valeric phase. This stream, 10, is then sent to the decanter where the aqueous phase and valeric phase, 12, are separated by decantation. The aqueous phase, 11, is recycled to the cell loop and the valeric phase, 12, containing the products (mainly dodecanedioic acid) is sent to a refining operation. The aqueous phase, 11, containing the cerium salts and most of the ruthenium is recycled back to the cell loop. Any gases are vented, 13, and can be scrubbed to recover ruthenium and valeric acid.

The cell, 14, is preferably a divided cell with a Nafion membrane, 15. An iridium oxide coating on titanium serves as the anode, 19, for oxidation of cerium +3. The valeric acid, cyclododecene and the aqueous solution are circulated at high velocity for good mixing and electrical efficiency. The cathode, 20, is an alloy such as Hastelloy. The cathode solution, 16, usually is dilute (5-30%) $H_2SO_4$ in water but may contain some nitric acid and other process materials, e.g., ruthenium, cerium and valeric acid. Hydrogen, 17, is the product from the cathode with small amounts of oxygen, 18, being generated in the anode compartment. Other cell materials can be used or selected by those skilled in the art, e.g., platinum electrodes, and other commercial membranes.

In order to reduce ruthenium tetroxide vapor losses, the oxygen, 18, from the anode is scrubbed with valeric acid (optionally with small amounts of cyclododecene in valeric acid) which is returned to the cell loop. Valeric acid is the preferred organic phase but a mixture of butyric and valeric acids can be used.

Different anodes may be used in this invention and include flat plates, wire mesh on flat plates and flat plates with perpendicular ridges (3 millimeters in height). The latter two designs increase the actual surface area (reduce current density) and improve efficiency. This invention is not limited by anode design or geometry.

The anode solutions can be prepared from cerium carbonate and/or cerium sulfate salt plus the appropriate acid. Normally the acidity as measured by pH is less than 1.

The process of the invention can be used to manufacture adipic acid from cyclohexene. The cyclohexene is fed into the two phase mixture described above. It is also possible to operate the process of the invention with a variation when making adipic acid from cyclohexene, since cyclohexene is sufficiently soluble in an aqueous solution comprising ruthenium tetroxide, cerium (+4) and cerium (+3) cations and at least one anion, selected from the group consisting of nitrate and bisulfate, the organic phase is unnecessary. The aqueous solution containing the dissolved cyclohexene can be subjected to electrolytic anodic oxidation at voltage greater than 1.5 volts at a temperature in the range of about 25 to 85 degrees C., and the cyclohexene is oxidized to adipic acid by the ruthenium tetroxide which is reduced to ruthenium dioxide, the ruthenium dioxide is reoxidized to tetroxide by the cerium (+4) which is reduced to cerium (+3) and the cerium is reoxidized to the (+4) by the anodic oxidation.

The process of this invention may be applied to cyclic olefins containing 5-15 carbons in the ring and the product recovered will be a dicarboxylic acid containing the same number of carbons. Examples 6 and 9 below, demonstrate the invention using cycloheptene and cyclooctene as the feed olefin.

EXAMPLES

An electrolytic cell with an iridium oxide coating on titanium anode with a planar area of 100 square centimeters, a Nafion membrane (100 cm$^2$) and a cathode of Hastelloy with an area of 100 cm$^2$ was used in these examples. The distance between anode and cathode was about 1.5 cm with the Nafion membrane equally spaced between the two electrodes. Turbulence promoters were used in each compartment. A DC power supply was connected to the cell and voltage and current could be varied over the range 1.3 v to 6.0 v and current from 1 amp to 30 amps.

The liquid (normally 20% $H_2SO_4$ in $H_2O$) in the cathode compartment was circulated with a centrifugal pump through the compartment and into a glass reservoir of 1-2 liter capacity which served as a gas liquid separator and a feed tank for the circulating pump. Hydrogen gas is normally evolved and vented. The pumping rate was about 5 gallons per minute. Some liquid can be removed from the loop if it is desired to maintain a constant liquid volume in this loop.

The liquid in the anode compartment was circulated in similar fashion through the anode compartment and one or two reservoirs were used in this loop. Cyclododecene or a solution of cyclododecene in valeric acid was pumped into the circulating liquid stream as it flowed from the reservoir(s) to the suction side of the circulating pump or pumps. The circulating rate was usually in the range 5-10 gallons per minute. Some oxygen gas is evolved and vented from liquid reservoirs. The liquid composition in the anode loop for each example will be given below. Liquid from the anode loop could be removed and valeric acid decanted from the aqueous phase and processed according to the specifications herein.

In each example after the aqueous phase was charged to the anode loop and being circulated voltage was applied and the dissolved cerium +3 was oxidized until the cerium +4 concentration reached an arbitrary level of 0.1-0.3N. At this point valeric acid and ruthenium (as sulfite or acetylacetonate) were added to the loop. The circulation provided very good mixing of the two phases and ruthenium was very rapidly oxidized to ruthenium tetroxide and distributed between the two phases.

Cyclododecene dissolved in valeric acid (10% by weight) was pumped into the anode loop at a rate so that the Ce +4 concentration was maintained relatively constant by the applied voltage and current. As the feed rate of cyclododecene was increased voltage and current were increased to maintain an arbitrary Ce +4 concentration preferably above 0.1N. The matching of feed rate with the current-voltage was quickly learned by experience so very little adjustment was required after the initial settings.

EXAMPLE 1

The anode loop was charged with 3897 grams of aqueous solution (d=1.25) which was comprised of dissolved cerium +3, nitrates and bisulfates with a pH of about 0.6. The cerium +3 concentration was 0.8N, the nitrate concentration was 1.8N, and the bisulfate was 1.2N assuming complete dissociation of the acid and salt species. The cathode loop was filled with aqueous 20% $H_2SO_4$ and circulation was started in both loops. By application of 1.8 volts and 10 amps for 1 hour and then 2.4 volts and 20 amps for 30 minutes the cerium +4 normality was 0.18. The temperature was maintained at 50° C. Valeric acid (300 ml) and 0.6 g ruthenium (as a water solution of ruthenium sulfite) were added to the circulating anode loop. A slight drop in Ce +4 normality occurs as the ruthenium sulfite and impurities in the commericial grade valeric acid are oxidized. A solution of 10% (wt.) cyclododecene in valeric acid was injected continously into the suction of the circulating pump while voltage was maintained at 2.5-2.6 v and current at 20.3-20.4 amps. The feed rate was 150 ml/hr. After one hour the Ce +4 normality was 0.122. Additional (0.2 g) ruthenium was added and the run continued for 60 minutes with 2.6 volts and 22 amps and 150 ml/hr. of 10% wt. cyclododecene in valeric acid. At the end of this period the Ce +4 normality was 0.122. The conversion of cyclododecene was essentially 100%.

Analysis showed that under these conditions dodecanedioic acid was made at a productivity of 3.1 lbs. per hour per square meter of membrane or planar electrode area. The power consumption was 1.9 KWhr per pound of dodecanedioic acid. The dodecanedioic acid selectivity as a measure of yield by gas chromatography was 85%. The in hand yield of dodecanedioic acid- was about 80%. Lower dibasic acids ($C_{11}$-$C_4$) were the major by-products.

EXAMPLE 2

The anode loop was charged with 3075 grams of aqueous solution (d=1.18) which was comprised of dissolved cerium +3 and nitrates with a pH of about 0.8. The cerium +3 concentration was 0.6N, the nitrate concentration was 2.8 assuming complete dissociation of the acid and salt species. The cathode loop was filled with aqueous 20% $H_2SO_4$ and circulation was started in both loops. By application of 2.8 volts and 20 amps for 30 minutes and then 2.2 volts and 10 amps for 60 minutes the cerium +4 normality was 0.17. Additional nitric acid (98 g of 70% $HNO_3$) was added to the anode loop. This lowered the pH to 0.7 and increased the nitrate concentration to 3.3N. The temperature was maintained at 50° C. Valeric acid (300 ml) and 0.6 g ruthenium (as a water solution of ruthenium sulfite) were added to the circulating anode loop. A slight drop in Ce +4 normality occurs as the ruthenium sulfite and impurities in the commercial grade valeric acid are oxidized. A solution of 10% (wt.) cyclododecene in valeric acid (density 0.927) was injected continuously into the suction of the circulating pump while voltage was maintained at 3.0 v and current at 20 amps. The feed rate was 120 ml/hr. After one hour the Ce +4 normality was 0.0942. Electrolysis continued for 60 minutes with 2.8-3.0 volts and 20 amps and 90 ml/hr. of 10% wt. cyclododene in valeric acid. At the end of this period the Ce +4 normality was 0.0995 and the pH was 0.7. The conversion of cyclododecene was essentially 100%.

Analysis showed that under these conditions dodecanedioic acid was made at a productivity of 2.0 lbs. per hour per square meter of membrane or planar electrode area. The power consumption was 2.9 KWhr per pound of dodecanedioic acid. The selectivity as a measure of yield by gas chromatography was 84.5% to dodecanedioic acid. The in hand yield of dodecanedioic acid was slightly over 80%. Lower dibasic acids ($C_{11}$–$C_4$) made up most of the by-products.

EXAMPLE 3

The anode loop was charged with 801 grams of aqueous solution (d=1.14) which was comprised of dissolved cerium +3 and bisulfate with a pH of about 0.8. The cerium +3 concentration was 0.3N, and the bisulfate was 1.2N assuming complete dissociation of the acid and salt species. The cathode loop was filled with aqueous 20% $H_2SO_4$ and circulation was started in both loops. By application of 2.8 volts and 20 amps for 20 minutes the cerium +4 normality was 0.21. The temperature was about 50° C. Valeric acid (50 ml), butyric acid (50 ml), and 0.2 g ruthenium (as a water solution (5 cc) of ruthenium sulfite) were added to the circulating anode loop. A slight drop in Ce +4 normality (0.21→0.17) occurs as the ruthenium sulfite and impurities in the commercial grade valeric acid are oxidized. A solution of 15% (wt.) cyclododecene in valeric acid was injected continuously into the suction of the anode circulating pump while voltage was maintained at 2.6 v and current at 20 amps. The temperature was 57° C. The feed rate was 60 ml/hr. After 30 minutes, the Ce +4 normality was 0.156. Additional (0.2 g) ruthenium was added and the run continued for 30 minutes at 56° C. with 2.8 volts and 20.1 amps. The feed was 60 ml/hr. of 15% wt. cyclododecene in valeric acid. At the end of this period the Ce +4 normality was 0.143. The conversion of cyclododecene was essentially 100%.

Analysis showed that under these conditions dodecanedioic acid was made at a productivity of 2.0 lbs. per hour per square meter of membrane or planar electrode area. The power consumption was 2.8 KWhr per pound of dodecanedioic acid. The selectivity as a measure of yield by gas chromography was 83% to dodecanedioic acid. The in hand yield of dodecanedioic acid was about 80%. Lower dibasic acids ($C_{11}$–$C_4$) made up most of the remaining products.

EXAMPLE 4

The anode loop was charged with 911 grams of aqueous solution (d=1.2) which was comprised of dissolved cerium +3, nitrates and bisulfates with a pH of about 0.6. The cerium +3 concentration was 0.7N, the nitrate concentration was 1.8N, and the bisulfate was 0.9N assuming complete dissociation of the acid and salt species. The cathode loop was filled with aqueous 20% $H_2SO_4$ and circulation was started in both loops. By application of 1.8 volts and 10 amps for 30 minutes, the cerium +4 normality was 0.21. The temperature was maintained at 50° C. Ruthenium (0.2 g as a water solution of ruthenium sulfite) was added to the circulating anode loop. A slight drop in Ce +4 normality occurs as the ruthenium sulfite is oxidized. A solution of 10% (wt.) cyclohexene in acetic acid was injected continuously into the suction of the circulating pump while voltage was maintained at 1.8 and current at 10.2 amps. The feed rate was 30 ml/hr. After one hour the Ce +4 normality was 0.23. Additional (0.2 g) ruthenium was added and the run continued for 60 minutes with 1.8 volts and 10.2 amps and 30 ml/hr. of 10% (wt.) cyclohexene in acetic acid. At the end of this period the Ce +4 normality was 0.26. The conversion of cyclohexene was essentially 100%.

Analysis showed that under these conditions adipic acid was made at a productivity of 1.0 lbs. per hour per square meter of membrane or planar electrode area. The power consumption was 1.9 KWhr per pound of adipic acid. The selectivity as a measure of adipic yield by gas chromography was 93%. The in hand yield of adipic acid was about 80%. Lower dibasic acids ($C_5$–$C_4$) were the major by-products.

EXAMPLE 5

(Control Example, Not an example of this invention.)

The anode loop was charged with 2407 grams of aqueous solution (d=1.35) which was comprised of dissolved cerium +3 methane sulfonate and methane sulfonic acid with a pH of about 0.1. The cerium +3 concentration was 1.1N, and the free methane sulfonic acid concentration was 3.3N. An additional 217 of methane sulfonic acid was added. The cathode loop was filled with aqueous 20% $H_2SO_4$ and circulation was started in both loops. By application of 2.6 volts and 20.1 amps for 60 minutes the cerium +4 normality was 0.21. The temperature was about 50° C. Valeric acid (200 ml), and 0.8 g ruthenium (as a water solution (20 cc) of ruthenium sulfite) were added to the circulating anode loop. A slight drop in Ce +4 normality occurs as the ruthenium sulfite and impurities in the commercial grade valeric acid are oxidized. A solution of 30% (wt.) cyclododecene in valeric acid was injected continuously into the suction of the anode circulating pump while voltage was maintained at 2.8 v and current at 20.2 amps. The temperature was 50° C. The feed rate was 30 ml/hr. After 60 minutes, the Ce +4 normality was 0.22. Additional (0.8 g) ruthenium was added and the run continued for 120 minutes at 50° C. with 2.8 volts and 20.2 amps. The feed was 30 ml/hr. of 30% wt. cyclododecene in valeric acid. At the end of this period the Ce +4 normality was 0.0943. The conversion of cyclododecene was essentially 100%. Note that the normality of Ce +4 was not constant but decreased from 0.21 →0.0943 indicating either the current-voltage must be increased or the feed rate decreased to maintain steady state.

Analysis showed that under these conditions dodecanedioic acid was made at an electrical productivity of about 1.7 lbs. per hour per square meter of membrane or planar electrode area. The power consumption was about 3.5 KWhr per pound of dodecanedioic acid. The selectivity as a measure of yield by gas chromography was 86% to dodecanedioic acid. The in hand yield of dodecanedioic acid was about 80%. Lower dibasic acids ($C_{11}$–$C_4$) made up most of the remaining products.

EXAMPLE 6

The anode loop was charged with 1366 grams of aqueous solution (d=1.25) which was comprised of dissolved cerium +3, nitrates and bisulfates with a pH of about 0.6. The cerium +3 concentration was 0.8N, the nitrate concentration was 1.8N, and the bisulfate was 1.2N assuming complete dissociation of the acid and salt species. The cathode loop was filled with aqueous 20% $H_2SO_4$ and circulation was started in both loops. By application of 2.2 volts and 10 amps for 1 hour the cerium +4 normality was 0.277. The temperature was maintained at 48° C. Valeric acid (100 ml) and 0.2 g ruthenium (as a water solution of ruthenium sulfite) were added to the circulating anode loop. A slight drop in Ce +4 normality occurs as the ruthenium sulfite and impurities in the commercial grade valeric acid are oxidized. In this example the Ce +4 normality was 0.218. A solution of 10% (wt.) cycloheptene in valeric acid was injected continuously into the suction of the circulating pump while voltage was maintained at 2.4 v and current at 10.0 amps. The feed rate was 45 ml/hr. After one hour the Ce +4 normality was 0.215. Additional (0.2 g) ruthenium was added and the run continued for 60 minutes with 2.4 volts and 10 amps and 45 ml/hr. of 10% wt. cycloheptene in valeric acid (density of 0.92 g/ml). At the end of this period the Ce +4 normality was 0.175. The conversion of cycloheptene was essentially 100%.

Analysis showed that under these conditions heptanedioic acid was made at a productivity of 0.9 lb. per hour per square meter of membrane or planar electrode area. The power consumption was 2.7 KWhr per pound of heptanedioic acid. The heptanedioic acid selectivity as a measure of yield by gas chromatography was 80%. The in hand yield of heptanedioic acid was about 70%.

EXAMPLE 7

The anode loop was charged with 1349 grams of aqueous solution (d=1.25) which was comprised of dissolved cerium +3, nitrates and bisulfates with a pH of about 0.6. The cerium +3 concentration was 0.8N, the nitrate concentration was 1.8N, and the bisulfate was 1.2N assuming complete dissociation of the acid and salt species. The cathode loop was filled with aqueous 20% $H_2SO_4$ and circulation was started in both loops. By application of 2.2 volts and 10 amps for 1 hour the cerium +4 normality was 0.30. The temperature was maintained at 50° C. Valeric acid (100 ml) and 0.2 g ruthenium (as a water solution of ruthenium sulfite) were added to the circulating anode loop. A slight drop in Ce +4 normality occurs (0.30→0.26N) as the ruthenium sulfite and impurities in the commercial grade valeric acid are oxidized. A solution of 10% (wt.) cyclohexene in valeric acid was injected continuously into the suction of the circulating pump while voltage was maintained at 2.0 v and current at 10 amps. The feed rate was 45 ml/hr. (4.1 g cyclohexene/hr.). After one hour the Ce +4 normality was 0.18. Additional (0.2 g) ruthenium was added and the run continued for 60 minutes with 2.2 volts and 10 amps and 45 ml/hr. of 10% wt. cyclohexene in valeric acid. At the end of this period the Ce +4 normality was 0.05. The conversion of cyclohexene was essentially 100%.

Analysis showed that under these conditions adipic acid was made at a productivity of 1.0 lb. per hour per square meter of membrane or planar electrode area. The power consumption was 2.2 KWhr per pound of adipic acid. The adipic acid selectivity as a measure of yield by gas chromatography was 83%. The in hand yield of adipic acid was about 70%. Lower dibasic acids ($C_5$-$C_4$) were the major by-products.

EXAMPLE 8

The anode loop was charged with 1343 grams of aqueous solution (d=1.25) which was comprised of dissolved cerium +3, nitrates and bisulfates with a pH of about 0.6. The cerium +3 concentration was 0.8N, the nitrate concentration was 1.8N, and the bisulfate was 1.2N assuming complete dissociation of the acid and salt species. The cathode loop was filled with aqueous 20% $H_2SO_4$ and circulation was started in both loops. By application of 2.2 volts and 10 amps for 1 hour the cerium +4 normality was 0.27. The temperature was maintained at 50° C. Ruthenium (0.2 g) (as a water solution of ruthenium sulfite) was added to the circulating anode loop. A slight drop in Ce +4 normality (0.27→0.24) occurs as the ruthenium sulfite is oxidized. Cyclohexene was injected continuously into the suction of the circulating pump while voltage was maintained at 2.0 v and current at 10 amps. The feed rate was 4 ml/hr. After one hour the Ce +4 normality was 0.23. Additional (0.2 g) ruthenium was added and the run continued for 60 minutes with 2.0 volts and 10 amps and 4 ml/hr. of cyclohexene. At the end of this period the Ce +4 normality was 0.22. The run continued for another hour at the same conditions. At the end of the period, the Ce +4 normality was 0.22. The conversion of cyclohexene was essentially 100%.

Analysis showed that under these conditions adipic acid was made at a productivity of 1.0 lb. per hour per square meter of membrane or planar electrode area. The power consumption was 2.0 KWhr per pound of adipic acid. The adipic acid selectivity as a measure of yield by gas chromatography was 93%. The in hand yield of adipic acid was about 82%. Lower dibasic acids ($C_5$-$C_4$) were the major by-products.

EXAMPLE 9

The anode loop was charged with 1594 grams of aqueous solution (d=1.25) which was comprised of dissolved cerium +3, nitrates and bisulfates with a pH of about 0.6. The cerium +3 concentration was 0.8N, the nitrate concentration was 1.8N, and the bisulfate was 1.2N assuming complete dissociation of the acid and salt species. The cathode loop was filled with aqueous 20% $H_2SO_4$ and circulation was started in both loops. By application of 2.2 volts and 10 amps for 1 hour the cerium normality was 0.25. The temperature was maintained at 48° C. Valeric acid (100 ml) and 0.2 g ruthenium (as a water solution of ruthenium sulfite) were added to the circulating anode loop. A slight drop in Ce +4 normality occurs as the ruthenium sulfite and impurities in the commercial grade valeric acid are oxidized (0.25→0.22). A solution of 10% (wt.) cis cyclooctene in valeric acid was injected continuously into the suction of the circulating pump while voltage was maintained at 2.3 v and current at 10 amps. The feed rate was 45 ml/hr. (4.1 g/hr. of cyclooctene). After one hour the Ce +4 normality was 0.26. Additional (0.2 g) ruthenium was added and the run continued for 60 minutes with 2.3 volts and 10 amps and 45 ml/hr. of 10% wt. cyclooctene in valeric acid. At the end of this period the Ce +4 normality was 0.27. The conversion of cyclooctene was essentially 100%.

Analysis showed that under these conditions octanedioic acid was made at a productivity of about 1.0 lbs. per hour per square meter of membrane or planar electrode area. The power consumption was 2.3 KWhr per pound of octanedioic acid. The octanedioic acid selectivity as a measure of yield by gas chromatography was 60%. The in hand yield of octanedioic acid was about 55%.

I claim:

1. A process for the oxidation of a cyclic olefin to a dicarboxylic acid which comprises adding the cyclic olefin to a two phase mixture comprising (a) an aqueous phase containing Ce(+4) and Ce(+3) cations, at least one anion selected from the group consisting of nitrate and bisulfate, and dissolved ruthenium tetroxide and (b) an organic phase containing an acid selected from the group consisting of butyric acid, valeric acid, hexanoic acid, 2-ethyl hexanoic acid and mixtures of such acids, and dissolved ruthenium tetroxide, while subjecting the mixture to an electrolytic anodic oxidation at a voltage greater than 1.5 volts and at a temperature in the range of about 25 to 85 degrees C.

2. The process of claim 1 in which the cyclic olefin is selected from the group consisting of cyclododecene, cyclohexene, cycloheptene and cyclooctene.

3. A process for the oxidation of cyclohexene to adipic acid which comprises adding cyclohexene to an aqueous solution comprising ruthenium tetroxide, cerium(+4) and cerium(+3) cations and at least one anion, selected from the group consisting of nitrate and bisulfate, while subjecting the solution to an electrolytic anodic oxidation at a voltage greater than 1.5 volts and at a temperature in the range of about 25 to 85 degrees C.

4. The process of claim 1 in which the concentration of Ce +4 is maintained at greater than 0.02N in the aqueous phase by appropriate control of electrode current density, cell voltage and cyclic olefin feed rate.

5. The process of claim 1 in which the volume ratio of aqueous phase to organic phase is in the range of 1 to 1 to 20 to 1.

6. The process of claim 1 which includes the additional subsequent steps of separating some of the organic phase from the aqueous phase and then re-contacting the separated organic phase with a small portion of the aqueous phase.

7. The process of claim 1 in which the aqueous phase contains total cerium +3 and +4 concentration above 0.2N and nitrate above 0.5N and bisulfate above 0.3N and has a pH of not more than 1.

8. The process of claim 7 in which the total cerium+3 and Ce +4 is above 0.2N and the combined anion concentration of one or more of the anions, nitrate and bisulfate, is in the range of 3-5 times the concentration of cerium.

9. The process of claim 1 in which cyclohexene is the cyclic olefin and the dicarboxylic acid is adipic acid.

10. The process of claim 1 wherein the cyclic olefin contains 5-15 carbons and the dicarboxylic acid contains the same number of carbons.

* * * * *